United States Patent [19]

Camerini Porzi

[11] Patent Number: 4,849,625
[45] Date of Patent: Jul. 18, 1989

[54] DEVICE, APPLICABLE TO OVENS, FOR MONITORING THE COLOR OF COFFEE AND SIMILAR COMMODITIES DURING THE COURSE OF A ROAST

[75] Inventor: Pier Cesare Camerini Porzi, Casalecchio di Reno, Italy

[73] Assignee: Officine Vittoria S.p.A., Bologna, Italy

[21] Appl. No.: 277,149

[22] Filed: Nov. 29, 1988

[30] Foreign Application Priority Data

Dec. 4, 1987 [IT] Italy .................. 3721 A/87

[51] Int. Cl.4 .................. G01J 3/50; H05B 1/02
[52] U.S. Cl. .................. 250/226; 219/502; 356/425
[58] Field of Search .................. 250/226; 99/286; 356/402, 407, 425; 426/523, 231, 233; 219/502

[56] References Cited

U.S. PATENT DOCUMENTS

| | | | |
|---|---|---|---|
| 2,436,575 | 2/1948 | Johnson | 219/502 |
| 2,572,678 | 10/1951 | Torres | 219/502 |
| 3,576,646 | 4/1971 | Alwood | 250/226 |
| 3,606,829 | 9/1971 | Alwood | 219/502 |
| 3,735,143 | 5/1973 | Langford | 350/226 |
| 4,057,352 | 11/1977 | Babb | 250/226 |
| 4,271,603 | 6/1981 | Moore, III | 99/286 |
| 4,325,191 | 4/1982 | Kumagai et al. | 99/286 |
| 4,350,442 | 9/1982 | Arild et al. | 356/407 |
| 4,642,906 | 2/1987 | Kaatze et al. | 99/286 |

FOREIGN PATENT DOCUMENTS

12551A/80  3/1980  Italy .

Primary Examiner—David C. Nelms
Assistant Examiner—Stephone B. Allen
Attorney, Agent, or Firm—Balogh, Osann, Kramer, Dvorak, Genova & Traub

[57] ABSTRACT

The device makes use of at least one photoemitter and at least one photodetector, operating in conjunction with the inspection glass of the oven against which the coffee beans tumble continually throughout the roast; the photodetector is located remotely, and receives its light input through an optic fiber link the transmitting end of which is supported, together with the photoemitters, by a block fitted to the discharge hatch of the oven directly over the inspection glass and invested with a coolant in order to maintain the temperature at the monitoring location within the preferred operating limits specified for the photoemitters and the optic fiber material.

7 Claims, 2 Drawing Sheets

DEVICE, APPLICABLE TO OVENS, FOR MONITORING THE COLOR OF COFFEE AND SIMILAR COMMODITIES DURING THE COURSE OF A ROAST

BACKGROUND OF THE INVENTION

The invention relates to a device for application to ovens which serves to monitor the color of a commodity, in particular coffee and similar edible products, during the course of a roast.

It is of paramount importance, when roasting coffee and similar commodities on any appreciable scale, that the condition of the commodity be monitored continuously and accurately, in order to permit of terminating the roast at the right moment.

To this end, roasting ovens, and indeed ovens in general, are provided with an inspection glass through which it is possible to verify the color of the charge visually. The color of the commodity will in fact vary as the roast progresses, changing from a light shade, of green in the case of coffee, to an increasingly dark brown.

Visual control alone being insufficient in the case of coffee, the same applicant has already set forth a device (see Italian application No. 12551 A/80) capable of monitoring the color of the beans and relaying a relative signal to a processing unit. The device in question consists in a shroud type housing, offered to the inspection glass by way of its open front and secured to the surrounding panel with a flange, which accommodates photoemissive and photodetector elements the outputs of which are fed into one input of an AND gate; the remaining input of the AND gate receives the output signals from an additional set of photoemissive and photodetector elements that sense the color of a reference sample of the correctly roasted product. Utilizing such a system, the moment that the color of the roasting commodity matches the sample color, a signal will be gated by the AND circuit to shut off the oven. Operation of the device outlined above is beset by a number of problems, however, first among which is the difficulty of ensuring accurate monitoring of the color of the beans when roasting.

More exactly, the photoemitters and photodetectors are highly sensitive to changes in temperature and, given that the device is installed in such close proximity to a heat source, both become prone to error in measure commensurate with the temperature to which they are exposed.

To limit such error, the flange of the shroud is located at a suitable distance from the surface of the oven, in order to expose the interior to the surrounding atmosphere and allow a certain degree of ventilation; external cooling fins are also incorporated, together with a toroidal duct through which air is able to circulate.

Nonetheless, air cooling of this order is neither sufficiently dependable, nor adjustable to suit the different temperature levels to which the device becomes subject during the various roasting steps. Moreover, the photodetectors are connected to the AND gate by way of means designed to correct the signal according to the prevailing temperature, and such means are themselves effected by the inherent inaccuracy of the various photoelectric elements. This much said, the distance between the shroud and the inspection glass cannot be determined solely by the need to ventilate the photoelectric elements, but most also be a function of the amount of light penetrating the shroud. In effect, ambient light can modify the color of the beans tumbling against the inside surface of the inspection glass, and in consequence, the response of the photodetectors becomes affected in a manner that is unforeseeable, and, like the temperature-related errors already mentioned, in no way preventable.

Accordingly, the object of the present invention is to overcome the drawbacks outlined above.

SUMMARY OF THE INVENTION

The stated object is achieved with a monitoring device as disclosed, in which the photodetector element is installed remotely from the insepection glass of the oven and associates therewith by way of light transmitting means one end of which is located in close proximity to the inspection glass, hence to the charge being monitored for color, and supported together with the photoemitter elements in a block invested externally by a liquid coolant. The output signal from the photodetector element is compared with the variable output of, or processed by, a colorimeter, prior to being received by a controller to which operation of the roasting oven is interlocked.

A first advantage of the device according to the present invention is that of the accuracy of color monitoring effected on the commodity during the roast, obtained by virtue of the fact that the photodetector element is installed in a location where the temperature is equal to its recommended operating temperature, and therefore remains free from thermally-induced error. The same applies in the case of the photoemitter elements (which in any case are better able to withstand thermal shock of a certain magnitude), as these are maintained at their correct operating temperature by the coolant, the temperature of which is easily controlled.

A further advantage of the device is its simplicity in design and operation, achieved by virtue of the fact that no use is made of compelx and delicate components to correct the thermally-induced errors referred to above.

Another advantage of the device is that of its versatility and flexibility in operation, obtained by inclusion of a colorimeter the output of which can be set to reflect either a prescribed roast characteristic of the end product, or the amount of heat to be applied during the roast step.

BRIEF DESCRIPTION OF THE DRAWINGS

The invention will now be described in detail, by way of example, with the aid of the accompanying drawings, in which.

DESCRIPTION OF THE PREFERRED EMBODIMENT

Figure 1:
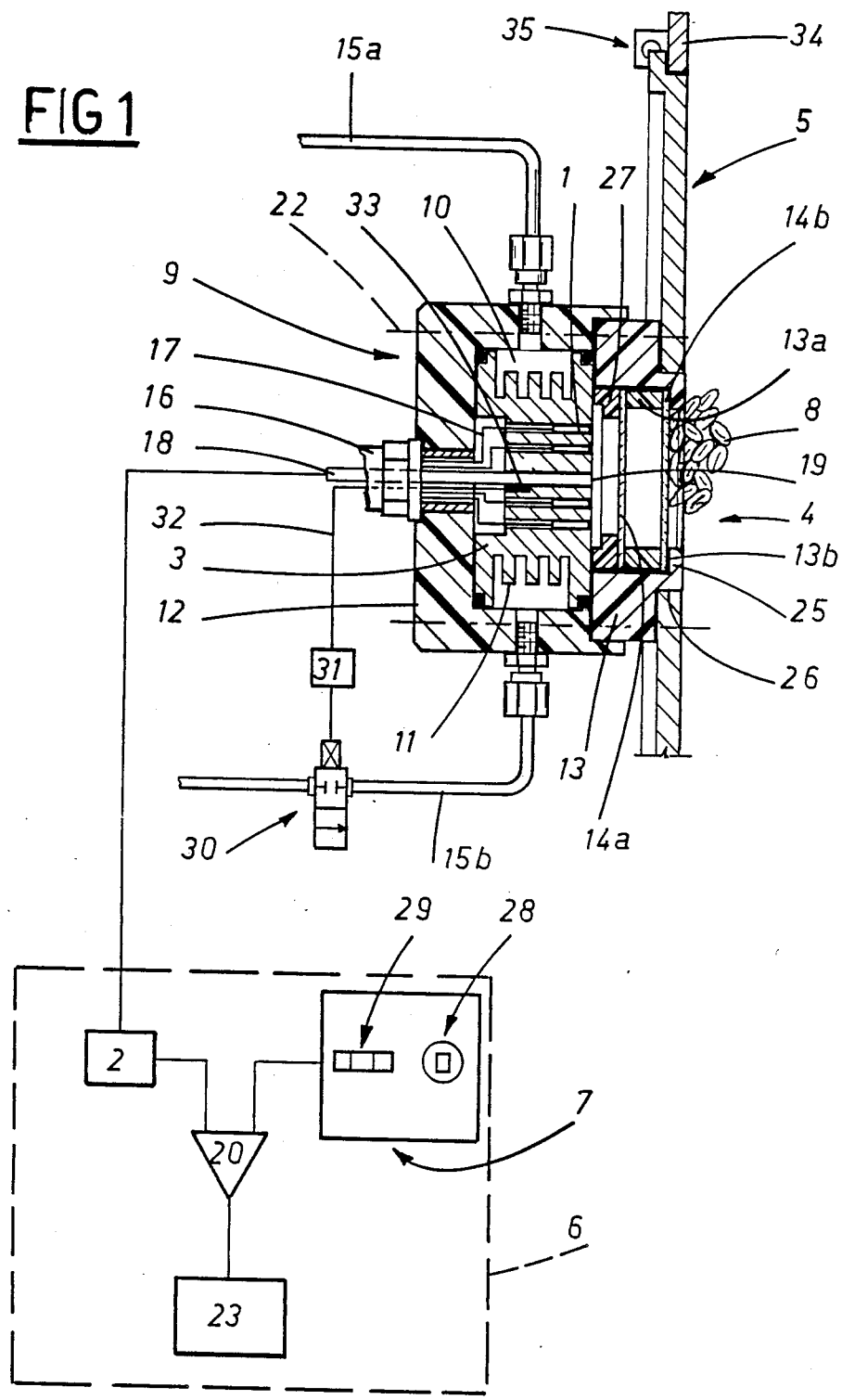
FIG. 1 is a schematic representation of the device disclosed, viewed in axial section.

With reference to FIG. 1, a device according to the invention is of the type fitted to the inspection glass 4 of a roasting oven, located at a point with whihc the commodity 8 is continuously in contact; such devices comprise at least one photoemitter element 1 and at least one photodetector element 2 operating in close proximity to the glass 4.

According to the invention, the photodetector 2 is positioned remote from the inspection glass 4, and linked to it by way of light transmitting means 18, embodied as a bundle of optic fibers.

The end 19 of the bundle 18 nearest the glass 4 is supported, together with the photoemitters 1, by a substantially cylindrical block 3 embodied with a central cylindrical section that is of diameter no greater than that of the endmost sections on either side, and embodied with fins 11 that are invested by a liquid coolant, for example water.

Figure 2:
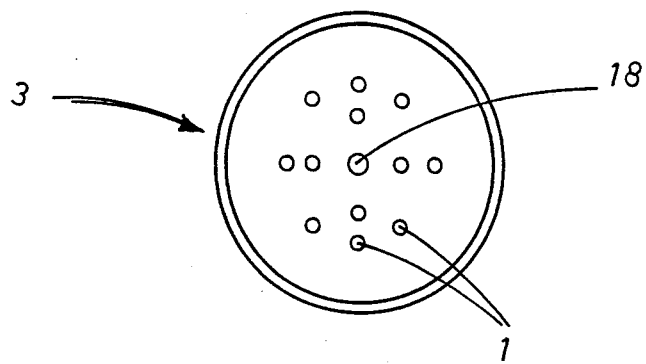
FIG. 2 is a front view of one of the components illustrated in FIG. 1.
Figure 3:
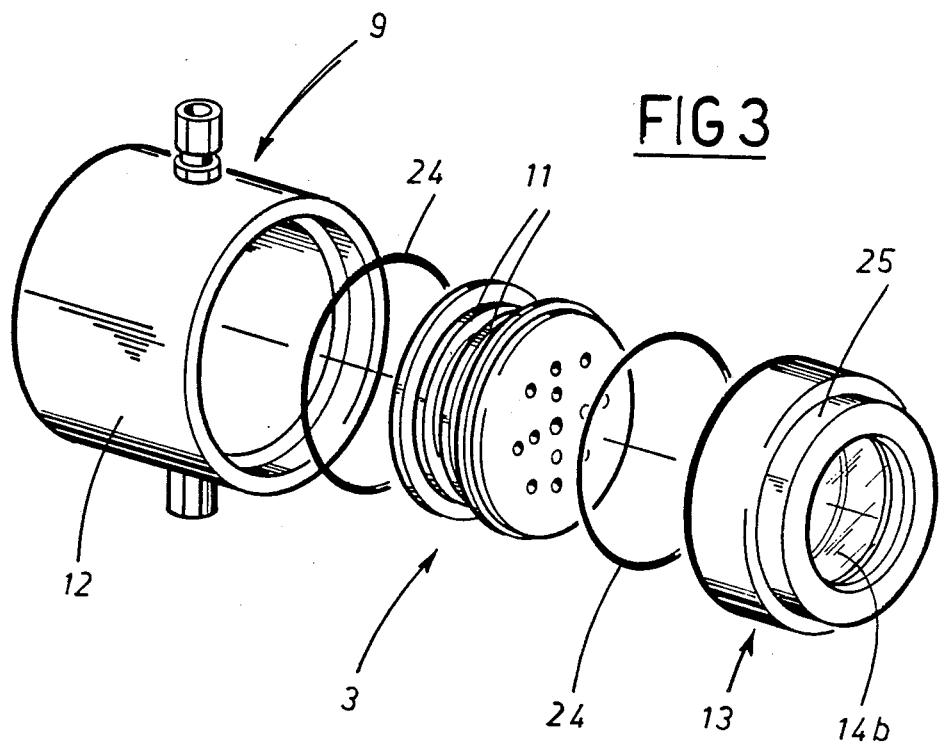
FIG. 3 is an exploded view of the device illustrated in FIG. 1.

The end 19 of the bundle 18 and the photoemitters 1 are accommodated by the block 3 in an axial hole at center, and a plurality of essentially longitudinal and radially distributed holes, respectively (see also FIG. 2).

The block 3 is fashioned from a material with good thermal conduction properties and lodged in a fluid-tight fit, ensured by conventional seals 24, internally of a housing 9 of opaque material that consists in a shroud 12 and a relative cover 13; more exactly, the block 3 and the shroud 12 combine to create an annular chamber 10.

Also associated with the shroud 12 are means 16 by which the light transmitting optic fibers 18 are ensheathed and protected, means 17 by which power is supplied to the photoemitters 1, and means 15, disposed at diametrically opposed points of the housing 9, by which fluid is ported into and away from the annular chamber 10.

The cover 13 is recessed a given distance into the shroud 12 in order to retain the block 3 in its correct position, and secured by means of fasteners denoted 22, which pass through both the shroud and the cover and engages in the panel of the oven that surrounds the inspection glass 4.

According to the invention, the cover 13 is hollow centered, and embodied with a spigot 25 designed to locate in a corresponding socket 26 afforded by the discharge hatch 5 of the oven. The hollow center is bridged by a pair of heat-resistant lenses 14a and 14b, which can be fitted by any conventional means; in FIG. 1, for example, the lens denoted 14a locates against one side of a distance ring 13a and is held in place by a retaining ring 27 breasted with the cylindrical block 3, whilst the lens denoted 14b is lodged between an inner rim 13b of the spigot 25 and the other side of the distance ringe 13a. Thus, a device according to the invention incorporates an inspection glass, in the shape of the lenses, as an integral part.

With a housing 9 thus embodied, the cover 13 is offered to the hatch 5 and the shroud 12 to the cover 13, whereupon the fasteners 22 (e.g. screws) can be inserted and tightened; thus, the shroud 12 is urged against the block 3, and the block against the retaining ring 27 and the lenses 14a, 14b, and the entire asesmbly is clamped to the hatch 5 in a single operation.

Also illustrated in FIG. 1, for additional clarity, is the wall 34 of the oven, from which the hatch 5 is suspended on hinges 35.

Still referring to FIG. 1, the remaining end of the means 16, a flexible tube for example, by which the optic fibers 18 and the photoemitter power supply means 17 are ensheathed and protected, is connected to a processing unit 6 located remotely from the roasting oven. The unit incorporates at least one photodetector element 2, also, a comparator 20, a colorimeter 7, and a controller 23 to which the operation of the oven is interlocked; it will be seen that the comparator 20 is in receipt of the output signals from the photodetector 2 and the colorimeter 7, and that its own output signal is cascaded into the controller 23.

The photodetector 2 is designed to determine the color of the light transmitted to it through the optic fibers 18 and produce an electrical signal that is a function of the detected color. The light transmitted is in fact none other than the light generated by the photoemitters 1, which is directed at the roasting commodity 8 and reflected back to the fibers in a frequency band that is a function of the color reached by the commodity 8. Thus, the contingency of disturbance from ambient light is eliminated completely, by virtue of the fact that the photoemitters 1 operate in an environment totally enclosed by the housing 9 and the hatch 5, and the photodetector 1 is enclosed in the remote processing unit 6.

The colorimeter 7 is of a type designed to produce an output signal proportional to a given color, selected by way of a control 28; the meter also comprises a display 29 by means of which to monitor the effective color of the commodity 8 continuously as the roast progresses.

The comparator 20 is designed such that receipt of matching input signals from the photodetector 2 and the colorimeter 7 will cause an output signal to be generated and relayed to the controller 23, which then shuts off the oven and triggers a signal used either to activate an operator warning facility or to set further automatic systems in motion.

The coolant portion means 15, hydraulic pipelines in the example illustrated, are connected with a solenoid operated valve 30, interlocked to control means 31 that are connected via a relative line 32 to a sender 33 located internally of and serving to sense the temperature registering in the support block 3. Accordingly, at a given temperature level of the block 3 as picked up by the sender 33 and relayed to the control means 33, the valve 30 will be piloted to operate and allow a proportioned flow of coolant through the annular chamber 10, thereby maintaining the block 3, hence the photoemitters 1 and the optic fibers 18, at a prescribed continuous temperature.

In a simple embodiment, the inlet line 15a of the porting means might be connected to the domestic water supply and the outlet line 15b to a waste. The foregoing specification implies no limitation; for example, the electrical circuit to which the photodetector 2 is connected might be differently embodied.

What is claimed is:

1. A device applicable to ovens, for monitoring the color of coffee and similar commodities during the course of a roast, comprising:
    at least one photoemitter, directed at an area of an inspection glass of the oven with which the monitored commodity remains contiguous during the course of the roast;
    at least one photodetector, positioned remotely from the inspection glass in a location the ambient temperature of which corresponds substantially to a preferred operating temperature of the photodetector;
    light transmitting means positioned between the photodetector and the inspection glass, the end of which nearest the inspection glass is supported, together with the photoemitters, by a block that is made fast to the panel of the oven adjacent the inspection glass and invested with a liquid coolant serving to maintain its temperature substantially at a level corresponding to the preferred operating temperature of the photoemitters and the light transmitting means;

means by which the output signal from the photodetector is compared with a given reference signal directly proportional to a prescribed color of the roasted end product, and relayed to a control means by which the oven will be shut off when the color of the roasted commodity monitored by way of the light transmitting means and the photodetector matches the prescribed color to which the reference signal is proportional.

2. A device as in claim 1, wherein the reference signal directly proportional to the prescribed color of the roasted end product is processed and emitted by a colorimeter.

3. A device as in claim 1, wherein the support block is fashioned from a material with good thermal conduction properties, substantially cylindrical in shape and exhibiting a finned central cylindrical section of diameter no greater than that of its two endmost sections, and accommodated by a housing in a fluid-tight fit in such a way that the housing and the block combine to create an annular chamber encompassing the fins and affording passage to a liquid coolant introduced by forced circulation.

4. A device as in claim 3, comprising:

a housing, composed of a shroud, encompassing the support block, and a relative cover exhibiting a hollow center;

an inspection glass, consisting in a pair of heat resistant lens accommodated by the hollow center of the cover in a fluid-tight fit;

fastening means passing longitudinally through the shroud and the cover and engaging in the structure of the oven;

means, associated with the shroud, by which the liquid coolant is ported into and away from the annular chamber;

means, associated with the shroud, that serve to ensheath and protect the light transmitting means;

means, passing into the shroud, by which power is supplied to the photoemitters.

5. A device as in claim 3, wherein the shroud and the cover are made fast to the discharge hatch of the oven.

6. A device as in claim 4, wherein the shroud and the cover are made fast to the discharge hatch of the oven.

7. A device as in claim 1, wherein the end of the light transmitting means offered to the inspection glass is disposed coaxial with the support block, and the photoemitter occupy positions that are substantially longitudinal and radially disposed about the axis of the block.

* * * * *